United States Patent
Schnell

(10) Patent No.: US 9,211,385 B2
(45) Date of Patent: Dec. 15, 2015

(54) TRACHEOSTOMY CANNULA WITH WINDOW

(75) Inventor: Ralf Schnell, Seligenstadt (DE)

(73) Assignee: TRACOE medical GmbH, Nieder-Olm (DE)

( * ) Notice: Subject to any disclaimer, the term of this patent is extended or adjusted under 35 U.S.C. 154(b) by 326 days.

(21) Appl. No.: 12/944,374

(22) Filed: Nov. 11, 2010

(65) Prior Publication Data
US 2011/0114097 A1    May 19, 2011

(30) Foreign Application Priority Data

Nov. 13, 2009 (DE) .......................... 10 2009 046 703
Dec. 11, 2009 (DE) .......................... 10 2009 054 573

(51) Int. Cl.
*A61M 16/00* (2006.01)
*A61M 16/04* (2006.01)

(52) U.S. Cl.
CPC ....... *A61M 16/0465* (2013.01); *A61M 16/0427* (2014.02); *A61M 16/0468* (2013.01); *A61M 16/0434* (2013.01); *A61M 16/0488* (2013.01)

(58) Field of Classification Search
CPC ......... A61F 5/08; A61M 16/00; A61M 16/06; A61M 16/208; A61M 15/00; A61M 16/0488; A61M 16/04; A61M 25/007; A61M 16/0402; A61M 16/0427–16/0431; A61M 16/0461–16/0463; A61M 16/0465–16/0472; A61M 16/0486; A61M 16/0497; A61M 16/0605; A61M 16/0627; A61M 16/0683–16/0694
USPC ............. 128/207.14–207.17, 200.24, 200.26; 604/264, 266
See application file for complete search history.

(56) References Cited

U.S. PATENT DOCUMENTS

| | | | | |
|---|---|---|---|---|
| 4,315,505 A | * | 2/1982 | Crandall et al. | 128/200.26 |
| 4,330,497 A | * | 5/1982 | Agdanowski | 264/150 |
| 4,633,864 A | * | 1/1987 | Walsh | 128/207.15 |
| 4,852,565 A | | 8/1989 | Eisele | |
| 4,990,143 A | * | 2/1991 | Sheridan | 604/526 |
| 5,305,742 A | * | 4/1994 | Styers et al. | 128/207.17 |
| 5,313,939 A | * | 5/1994 | Gonzalez | 128/207.14 |
| 6,722,367 B1 | * | 4/2004 | Blom | 128/207.14 |
| 7,341,061 B2 | * | 3/2008 | Wood | 128/207.29 |
| 2009/0156953 A1 | * | 6/2009 | Wondka et al. | 600/538 |

FOREIGN PATENT DOCUMENTS

DE    102006035887 A1    2/2008
WO       2008144589 A1    11/2008

* cited by examiner

*Primary Examiner* — Jason Flick
*Assistant Examiner* — Ned T Heffner
(74) *Attorney, Agent, or Firm* — Paul & Paul

(57) ABSTRACT

The present invention concerns a tracheostomy cannula comprising a cannula tube, wherein the cannula tube has a bend with a radially inward and a radially outward side of the cannula tube and a tube lumen and a tube wall and an axis extending parallel to the tube wall in the tube lumen and a distal and a proximal end and on the radially outward side of the bend a first window region having one or more openings in the tube wall. To provide a tracheostomy cannula having a cannula tube, with which talking is made possible and the entry of air into the tissue is prevented even when the position of the tracheostomy cannula in the trachea or the anatomical conditions change, it is proposed in accordance with the invention that the cannula tube has in axially displaced relationship with the first window region at least one further window region having one or more openings in the tube wall.

22 Claims, 3 Drawing Sheets

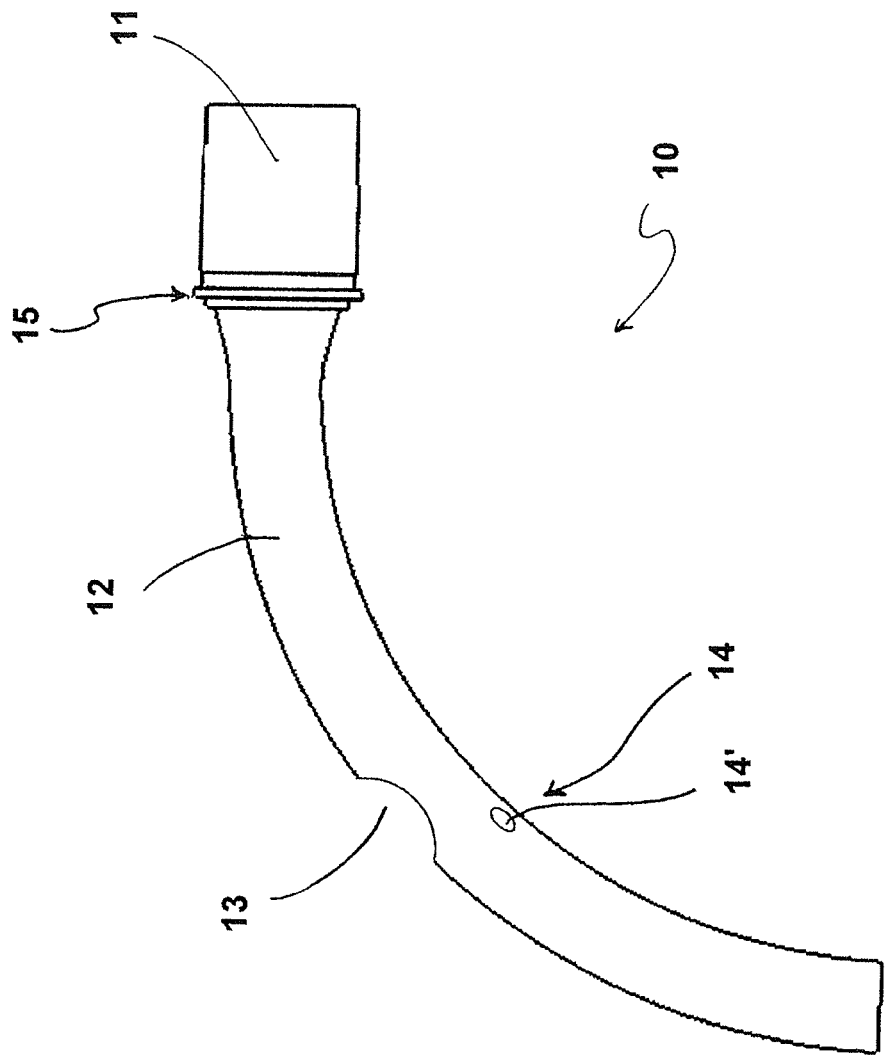

TRACHEOSTOMY CANNULA WITH WINDOW

BACKGROUND OF THE INVENTION

The present invention concerns a tracheostomy cannula comprising a cannula tube, wherein the cannula tube has a bend with a radially inward and a radially outward side of the cannula tube and a tube lumen and a tube wall and an axis extending parallel to the tube wall in the tube lumen and a distal and a proximal end and a first window region having one or more openings in the tube wall.

Patients having a tracheostoma, in whom the larynx is partially or completely preserved, are generally capable of talking. It will be noted however that for that purpose air must pass from the trachea upon exhalation into the region of the larynx. That is not possible in the case of tracheostomy cannulas having a closed cannula tube as the air passes through the cannula tube exclusively into the trachea, the bronchial tubes and the lungs and back in the same way.

In order nonetheless to permit patients with a larynx to talk, tracheostomy cannulas are used, in which the cannula tube has a window region. In that region the tube wall of the cannula tube is apertured by one or more openings. If during the exhalation process the tube lumen of the cannula tube is closed at the proximal end by a valve or by being covered with a finger, the exhaled air cannot escape through the proximal end of the tracheostomy cannula but passes through the window region to the larynx so that the patient can talk.

In that respect the terms 'distal' and 'proximal' are used from the point of view of a physician performing treatment, that is to say the proximal end of the tracheostomy cannula or the cannula tube is outside the body of the patient while in the inserted condition of the tracheostomy cannula the distal end is in the interior of the trachea.

Although tracheostomy cannulas are generally individually selected, it can happen due to slipping upon movement or a change in the anatomical conditions, for example due to the wound healing, that the window region is not free in the trachea but bears against the trachea wall or surrounding tissue. In those cases the patient cannot speak or can speak only with a very great effort. In addition particularly in the case of freshly operated patients there is the risk that the window region comes to lie in the stoma region and air passes into the tissue, resulting in the formation of emphysemas.

To resolve that problem, it has already been proposed in DE 10 2006 035 887 that a tracheostomy cannula is inserted, the effective length of the external cannula and/or the internal cannula of which is variable. By using such tracheostomy cannulas it is possible to position the window region of the cannula in such a way that the position is optimally adapted to the respective anatomical conditions.

SUMMARY OF THE INVENTION

In comparison with that state of the art the object of the present invention is to provide a tracheostomy cannula having a cannula tube, with which, even if the position of the tracheostomy cannula in the trachea or the anatomical conditions change, speech is made possible and the penetration of air into the tissue is prevented.

According to the invention that object is attained in that the cannula tube has in axially displaced relationship with the first window region at least one further window region having one or more openings in the tube wall.

The further window region is arranged on the cannula tube in axially displaced relationship with the first window region so that talking is possible by means of the air escaping from the further window region if the first window region bears against the trachea or the adjoining tissue or vice-versa. In addition, penetration of the air into the tissue when the window region bears against the body tissue is prevented and thus the risk of emphysema formation is reduced by virtue of the air escaping through the exposed window region.

The window regions can each comprise one or more openings independently of each other, wherein the plurality of openings have a smaller opening cross-section than a single opening. If there are a plurality of openings they are desirably restricted to a certain region, the window region.

In certain embodiments the first window region and the further window region adjoin each other and preferably the first window region and the at least one further window region are spaced from each other.

The window regions can be of different dimensions and shapes. Preferably in that respect however a width dimension, measured in the peripheral direction (circumferential direction) of the cannula tube, of between about ¼ and ⅓ of the periphery (circumference), is not exceeded. Further preferably the axial dimension of a window region is between about ⅓ and ½ of the periphery (circumference) of the cannula tube. If the window region comprises a plurality of openings in the tube wall then the window region covered by the openings including the remaining intermediate spaces can be larger but preferably it is always of such a dimension that the entire window region can be exposed without direct contact with the body tissue in the trachea.

Preferably the first and/or the further window region is provided with a valve or a simple flap which covers the opening or openings and which only allows air to issue outwardly. That valve or flap prevents foreign bodies from passing into the tracheostomy cannula and thus into the trachea insofar as it closes the window region. Opening of the window region is effected only when the flap or the valve are pressed open by a corresponding internal pressure in the cannula tube.

In preferred embodiments the tracheostomy cannula can be provided for percutaneous tracheostomy, wherein the tracheostoma is enlarged or held open by means of an insertion aid and the tracheostomy cannula itself so that the latter can be introduced into the trachea through the tracheostoma.

In certain embodiments a plurality of further window regions are provided in the tube wall of the cannula tube, preferably there is precisely one window region in the wall of the cannula tube. The more window regions that there are, the correspondingly more problematical can the possible ingress of secretions and possibly solid bodies (for example chyme) into the tracheostomy cannula become. On the other hand a total of at least two window regions for functioning of the tracheostomy cannula according to the invention are required.

Preferably the further window region is arranged displaced relative to the first window region in the peripheral direction of the cannula tube about the axis thereof.

If one of the window regions bears against the trachea or the surrounding further body tissue, for example due to the tracheostomy cannula slipping in the tracheostoma or the trachea, then the axially and peripherally displaced arrangement of the window regions ensures with a high degree of probability that one or more window regions are exposed, whereby little or no air passes into the tissue at the window regions in contact with the trachea or surrounding tissue, and at the same time the patient is able to talk.

Preferably the first window region is arranged on the radially outward side or laterally of the bend of the cannula tube.

The bend in the cannula tube preferably describes an arc with an included angle of 100°, wherein deviations of up to +/−20° are included. If the first window region is arranged at the radially outward side of the bend then the center point of that window region is preferably substantially at the apex of the bend, that is to say in the case of a circular arc at about 50°±20° angle with respect to the end of the cannula. In the case of a tracheostomy cannula in the inserted condition, such a first window region comes to bear against the top side of the cannula tube in the region of the trachea.

Particularly preferably the further window region is arranged on the radially inward side of the bend of the cannula tube.

It has been found that this arrangement of a further window region affords a high level of certainty that at least one of the window regions is exposed in order in that way to retain the capability for the patient to speak even if one of the window regions bears against body tissue.

In a preferred embodiment of the invention the first and further window regions are arranged at diametrally mutually opposite sides of the cannula tube.

That has the advantage that, even in the case of a tracheostomy cannula which is displaced in some direction and in respect of which the first window region is blocked, speech can still be made possible.

In a preferred embodiment the first window region and/or the second window region has a plurality of openings in the tube wall.

The openings in the window regions can be of different sizes and shapes. Preferably in this embodiment the openings are substantially circular, wherein particularly preferably the diameter of the openings is between 2 and 3 mm. Such small openings prevent in particular foreign bodies from passing into the cannula tube of the tracheostomy cannula, but the resistance to exhalation is not increased or only immaterially increased. In addition the small openings can ensure that, when sucking away mucus and so forth from the cannula the sucker does not issue from the cannula through the window and injure the trachea wall. In addition when using windows of smaller openings less granulation tissue is formed at the openings, which otherwise can possibly block the cannula.

In a preferred embodiment the further window region is arranged displaced relative to the first window region by an amount of between 0.3 cm and 3 cm, preferably between 1 cm and 2 cm, axially in the direction of the distal end. In that respect it is assumed that there is a spacing between the furthest distally arranged opening of the first window region and the most closely adjacent proximally arranged opening of the further window region.

With that arrangement the probability of both window regions bearing against body tissue is particularly slight.

Particularly preferably the sum of the opening cross-sections of the one or more openings of the further window region is between 1/10 and 1/2, preferably between 1/5 and 1/3, of the area of the cross-section of the tube lumen at the proximal end. It has been shown that in the case of a cannula tube having a first window region and at least one further window region the opening cross-section of the openings of the further window region can be markedly smaller than the free cannula cross-section.

In a further preferred embodiment the opening cross-section of the one or more openings of the first and the further window region is respectively between 1/10 and 1/3 of the area of the cross-section of the tube lumen at the proximal end.

Due to the smaller opening areas the window regions in a preferred embodiment can be displaced further in the direction of the distal end of the cannula tube, in comparison with conventional tracheostomy cannulas with a window region. That prevents in particular emphysema formation in the region of the stoma.

A particularly preferred embodiment of the invention is one in which the cross-section of the one or more openings of the first window region is of substantially the same size as the cross-section of the one or more openings of the further window region. In that way two equivalent window regions are made available, which when one of the two window regions is blocked permits speech without major effort on the part of the patient.

A further preferred embodiment is characterised in that the tracheostomy cannula has a cuff which is arranged displaced axially in the direction of the distal end relative to the first and the further window region. Such cuffs are used in tracheostomy cannulas to prevent mucus or solid bodies such as for example remains of food passing along the cannula tube externally on the tracheostomy cannula into the trachea and finally into the lungs. Particularly in the case of dysphagia patients and patients with artificial respiration, that prevents aspiration of mucus or solid bodies.

By virtue of the arrangement of the cuff distally relative to the window regions, talking on the part of the patient is not prevented by the cuff and at the same time the tracheostomy cannula is pressed into a substantially central position within the trachea, thereby additionally preventing the first and further window regions from bearing against the trachea.

In a particularly preferred embodiment the tracheostomy cannula further has an inner cannula which can be inserted into the cannula tube and having a tube wall and a tube lumen, wherein the inner cannula has inner window regions corresponding to the first and further window regions of the cannula tube, with one or more openings in the tube wall, which in the axial direction respectively at least partially overlap with the first or the further window region of the cannula tube.

The advantage of a tracheostomy cannula having a cannula tube and an inner cannula is that, when talking is not required, the inner cannula with the tube wall with window regions can be replaced by an inner cannula without window regions. In addition, cleaning of the inner cannula and thus removal of any contamination in the tracheostomy cannula can be more easily effected in that the inner cannula is removed, with the cannula tube remaining in the tracheostoma. Such inner cannulas are of such a configuration that they are fitted into the tube lumen of the cannula tube and in particular terminate in the distal region sealingly with the cannula tube. In particular in that way it is possible to prevent secretions passing through the window regions from running down within the cannula tube into the trachea and finally into the lungs.

Preferably the window regions of the cannula tube with the one or more openings in the tube wall are so arranged that at least 50% and preferably at least 70% and particularly preferably at least 80% of the opening area of the inner window regions overlaps with the opening areas of the window regions in the cannula tube.

Preferably the opening cross-sections of the corresponding inner window regions are larger than the opening cross-sections of the respective window regions in the cannula tube.

Preferably the inner cannula with window region in the tube lumen bears snugly against the inside wall of the tube wall of the cannula tube. That prevents air from flowing along between the tube wall of the inner cannula and the tube wall of the cannula tube and thereby possibly increasing the resistance to respiration.

In a particularly preferred embodiment the corresponding inner window regions of the inner cannula each have precisely one opening in the tube wall.

Preferably that affords the possibility in combination with a cannula tube having window regions with a plurality of openings in the tube wall of providing a tracheostomy cannula in which an opening area of minimum size in the cannula tube which is provided by a plurality of openings of small diameters permits talking with a low level of air resistance even when the corresponding inner window regions of the inner cannula do not exactly coincide with the window regions of the cannula tube. That has particular advantages in terms of manufacture of the tracheostomy cannulas for it is possible in that way to use tracheostomy cannulas with a cannula tube of identical diameter for the tube lumen and an identical length but (slightly) different positions for the window regions together with a single kind of inner cannula.

In a further preferred embodiment an inner window region of the inner cannula has an opening and another inner window region has a plurality of openings corresponding to the openings of the window regions in the cannula tube.

BRIEF DESCRIPTION OF THE DRAWINGS

Further advantages, features and possible uses of the present invention will be apparent from the description hereinafter of preferred embodiments and the related Figures in which:

FIG. 3 shows an inner cannula as can be inserted into the cannula tube in FIG. 2.

DETAILED DESCRIPTION

Figure 1:
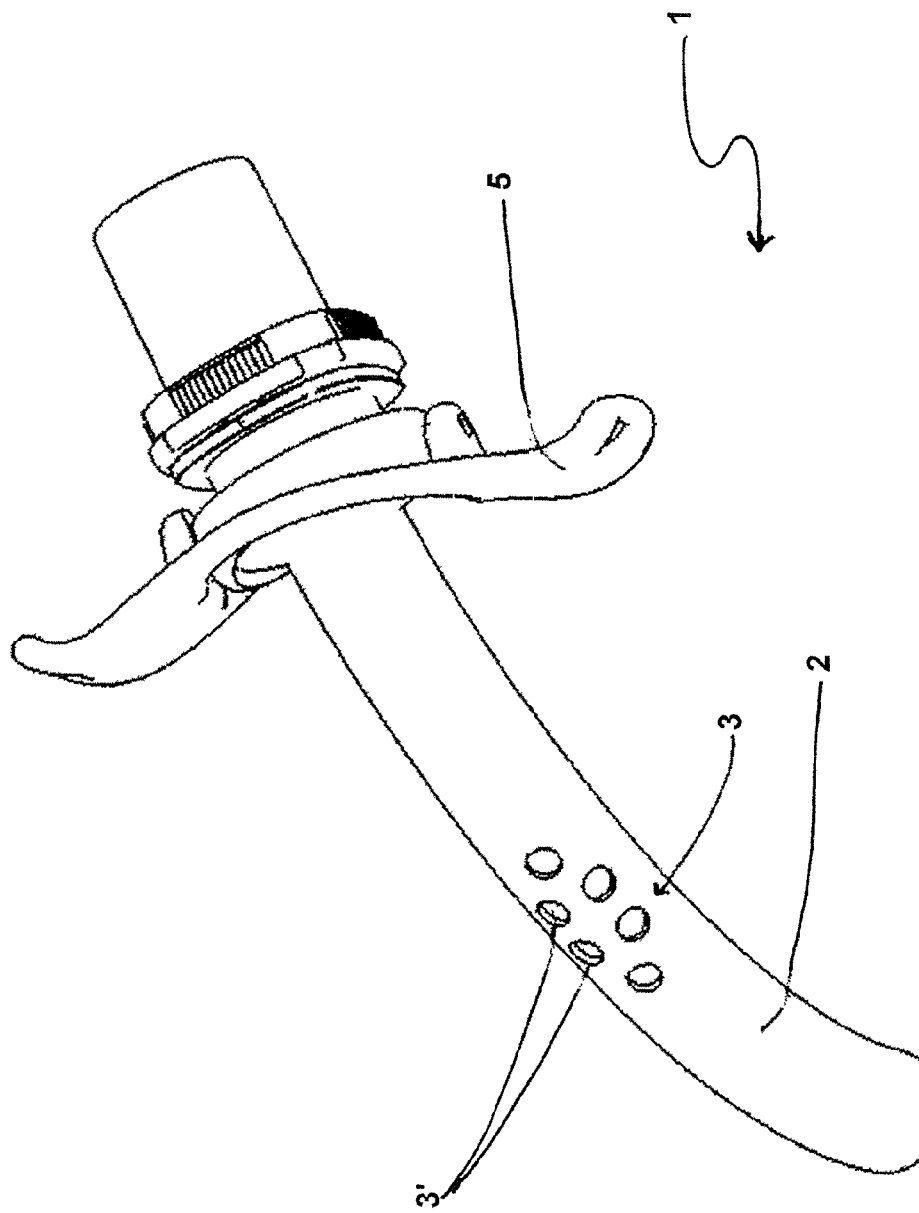
FIG. 1 shows a perspective view of a tracheostomy cannula with cannula tube in a plan view on to the radially outward side of the bend.

FIG. 1 shows a tracheostomy cannula referenced 1. It has a cannula tube 2 which in turn has a window region 3 at the radially outward side of the bend in the tube wall. The window region 3 comprises a total of six openings 3'. In relation to the window region 3, there is a further window region 4 which is arranged axially displaced relative to the window region 3 and displaced in the peripheral direction of the cannula tube about the axis in such a way that it is not visible in the perspective view shown in FIG. 1. Provided at the proximal end of the cannula tube 2 is a shield 5 which is provided to bear against the surface of the neck of a patient, around a tracheostoma.

Figure 2:
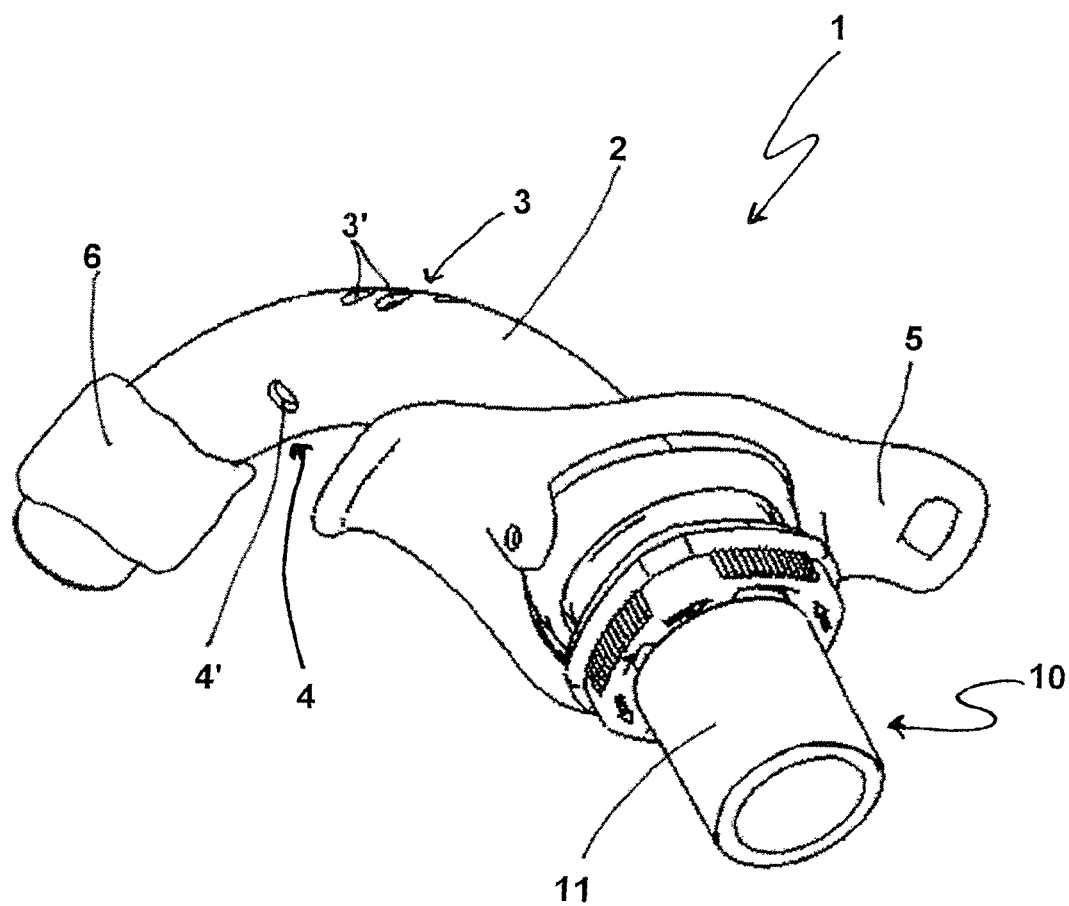
FIG. 2 shows a perspective view of a tracheostomy cannula with an inner cannula as a side view on to the bend of the cannula tube.

FIG. 2 shows a further embodiment of a tracheostomy cannula 1 according to the invention. The tracheostomy cannula has a cannula tube 2 with a first window region 3 and a further window region 4. The first window region comprises a plurality of openings of which three openings 3' are shown. The further window region 4 is arranged axially displaced relative to the first window region and is on the radially inward side of the bend in the cannula tube 2. The further window region comprises two openings of which one opening 4' is shown.

As in the embodiment shown in FIG. 1 the shield 5 serves for bearing against the surface of the neck of a patient, around a tracheostoma. It is at the proximal end of the cannula tube 3 of the tracheostomy cannula 1.

A cuff is arranged in distal relationship with the first window region 3 and the second window region 4. That cuff can be pumped up by way of a balloon (not shown) and filling hose after introduction of the tracheostomy cannula through a tracheostoma into the trachea. In that case the cuff bears with a slightly increased pressure against the trachea wall.

A part of an inner cannula 10 which is inserted into the cannula tube 2 can be seen at the proximal end of the tracheostomy cannula 1. That part is the connector 11, by means of which for example a speech valve which permits the inlet of air into the tracheostomy cannula but prevents exhalation through the opening of the tracheostomy cannula can be fitted.

FIG. 3 shows such an inner cannula 10, as can be used in the tracheostomy cannula shown in FIG. 2.

The inner cannula has a connector 11 with which a speech valve can be fixed in position. The inner cannula also has a tube 12 with tube wall and tube lumen, wherein a first window region 13 and a second window region 14 are provided in the tube wall. The first window region 13 includes a single opening. When the inner cannula is introduced into a cannula tube, as shown in FIG. 2, the inner window region 13 corresponds to the window region 3 of the cannula tube. The second window region comprises precisely two openings 14, of which one is shown. In the condition in which the inner cannula 10 is inserted into the cannula tube 1 the openings 14' correspond to the openings 4' of the cannula tube 1 shown in FIG. 2, in which respect the openings 14' in the inner cannula 10 are slightly larger than the openings 4' in the cannula tube 1.

The portion 15 represents an adaptor with which the inner cannula can be secured to a shield which is at the proximal end of a cannula tube.

For the purposes of the original disclosure it is pointed out that all features as can be seen by a man skilled in the art from the present description, the drawings and the appendant claims, even if they are described in specific terms only in connection with certain other features, can be combined both individually and also in any combinations with others of the features or groups of features disclosed here insofar as that has not been expressly excluded or technical aspects make such combinations impossible or meaningless. That also respectively applies in corresponding fashion for a plurality of features recited in an appendant claim, which can be respectively implemented individually insofar as they are not directly mutually dependent for technical reasons. A comprehensive explicit representation of all conceivable combinations of features is dispensed with here only for the sake of brevity and readability of the description.

The invention claimed is:

1. A tracheostomy cannula comprising an outer cannula tube,
　wherein the outer cannula tube has a bend with a radially inward side and a radially outward side of the outer cannula tube, and a tube lumen, and a tube wall and an axis extending parallel to the tube wall in the tube lumen, and a distal end and a proximal end, and a first window region having at least one opening in the side of the tube wall of the outer cannula tube,
　characterised in that the outer cannula tube has, in axially displaced relationship with the first window region, at least a second window region separate from the first window region having at least one opening in the tube side wall;
　the tracheostomy cannula being further characterised in that the tracheostomy cannula has an inner cannula tube having a tube wall and a tube lumen, which inner cannula tube can be inserted into the outer cannula tube;
　wherein the inner cannula tube has a first and second inner window regions corresponding to the first and the second window regions of the outer cannula tube and having at least one opening in the inner cannula tube wall which at least partially respectively overlaps in the axial direction with the respective first window region or the second window region of the outer cannula tube;

further characterised in that the distal portion of the inner cannula tube terminates in sealing engagement with the distal portion of the outer cannula tube, further characterised in that the second window region of the outer cannula tube is arranged displaced relative to the first window region of the outer cannula tube in the peripheral direction of the outer cannula tube about the axis thereof, and characterised in that at least one of the first window region and the second window region of the outer cannula tube have a plurality of openings in the tube wall.

2. A tracheostomy cannula as set forth in claim 1 characterised in that the first window region of the outer cannula tube is arranged on the radially outward side or laterally of the bend in the outer cannula tube.

3. A tracheostomy cannula as set forth in claim 1 characterised in that the second window region of the outer cannula tube is arranged on the radially inward side of the bend in the outer cannula tube.

4. A tracheostomy cannula as set forth in claim 1 characterised in that the first and the second window regions of the outer cannula tube are arranged at diametrally mutually opposite sides of the outer cannula tube.

5. A tracheostomy cannula as set forth in claim 1 characterised in that the window regions of the outer cannula tube have a width dimension, measured in the peripheral direction of the outer cannula tube, not exceeding about ⅓ of the periphery.

6. A tracheostomy cannula as set forth claim 1 characterised in that the cross-section of the at least one opening of the first window region of the outer cannula tube is of substantially the same size as the cross-section of the at least one opening of the second window region of the outer cannula tube.

7. A tracheostomy cannula as set forth in claim 1 characterised in that the tracheostomy cannula has a cuff which is arranged displaced axially in the direction of the distal end relative to the first and the second window regions.

8. The tracheostomy cannula of claim 1, wherein the axial dimension of a window region is between about ⅓ and ½ of the periphery of the cannula tube.

9. A tracheostomy cannula as set forth in claim 1 characterised in that the openings in the first window region of the outer cannula tube are smaller than the openings in the adjacent first window region of the inner cannula and that the openings in that second window region of the outer cannula tube are smaller than the openings in the adjacent second window region of the inner cannula, characterized in that the axial displacement of each respective second window region to the respective first window region provides for air to escape from the second window region if the first window region is mechanically block as it bears against the trachea or the adjoining tissue, or vice-versa, and further characterized that a penetration of air into the tissue when the window region bears against the body tissue is prevented thus, reducing the risk of emphysema formation by air escaping through the exposed portion of the window region.

10. A tracheostomy cannula as set forth in claim 1 characterised in that the inner cannula with its window regions bears snuggly against the inside wall of the outer cannula tube wall whereby air is prevented from flowing between the outer cannula tube wall and the inner cannula wall thereby avoiding increasing resistance to respiration.

11. A tracheostomy cannula as set forth in claim 1 characterised in that the at least one opening is substantially circular.

12. The tracheostomy cannula of claim 11, wherein the diameter of the openings is between 2 and 3 mm.

13. A tracheostomy cannula as set forth in claim 1 characterised in that the second window region of the outer cannula tube is arranged displaced relative to the first window region of the outer cannula tube axially in the direction of the distal end of the outer cannula tube by an amount of between 0.3 cm and 3 cm.

14. The tracheostomy cannula of claim 13, wherein in the outer cannula tube the second window region is arranged displaced relative to the first window region axially in the direction of the distal end by an amount of between 1 cm and 2 cm.

15. A tracheostomy cannula as set forth in claim 1 characterised in that the sum of the cross-section of any openings of the second window region of the outer cannula tube is between $1/10$ and $½$, of the area of the cross-section of the tube lumen at the proximal end of the outer cannula tube.

16. The tracheostomy cannula of claim 15, wherein the cross-section of at least one of the openings of the second window region of the outer cannula tube is between ⅕ and ⅓ of the area of the cross-section of the tube lumen at the proximal end.

17. The tracheostomy cannula of claim 15, wherein the opening cross-section of the at least one opening of the first and the second window regions of the outer cannula tube is respectively $1/10$ to ⅓ of the area of the cross-section of the tube lumen at the proximal end.

18. A tracheostomy cannula as set forth in claim 1, characterized in that there is at least 50% overlap between opening (s) of a window region of the inner cannula tube with opening (s) of a window region of the outer cannula tube.

19. The tracheostomy cannula of claim 18, wherein said overlap is at least 70%.

20. The tracheostomy cannula of claim 18, wherein said overlap is at least 70%.

21. A tracheostomy cannula as set forth in claim 1 characterised in that the corresponding inner window regions of the inner cannula tube each have precisely one opening in the tube wall.

22. The tracheostomy cannula of claim 21, wherein a corresponding inner window region of the inner cannula tube has an opening and another inner window region of the inner cannula tube has a plurality of openings corresponding to openings of a window region in the outer cannula tube.

* * * * *